(12) United States Patent
Zhu et al.

(10) Patent No.: US 12,178,525 B2
(45) Date of Patent: Dec. 31, 2024

(54) ORTHOPEDIC SURGICAL DEVICE AND ORTHOPEDIC SURGICAL ROBOT SYSTEM

(71) Applicant: SHENZHEN FUTURTEC MEDICAL CO., LTD., Shenzhen (CN)

(72) Inventors: Shengxiao Zhu, Shenzhen (CN); Ye Luo, Shenzhen (CN); Tao Zhang, Shenzhen (CN); Jiarui Chen, Shenzhen (CN)

(73) Assignee: SHENZHEN FUTURTEC MEDICAL CO., LTD., Shenzhen (CN)

( * ) Notice: Subject to any disclaimer, the term of this patent is extended or adjusted under 35 U.S.C. 154(b) by 462 days.

(21) Appl. No.: 17/622,772

(22) PCT Filed: Jul. 6, 2021

(86) PCT No.: PCT/CN2021/104851
§ 371 (c)(1),
(2) Date: Dec. 24, 2021

(87) PCT Pub. No.: WO2022/007817
PCT Pub. Date: Jan. 13, 2022

(65) Prior Publication Data
US 2022/0346892 A1    Nov. 3, 2022

(30) Foreign Application Priority Data
Jul. 6, 2020 (CN) .......................... 202010642040.1

(51) Int. Cl.
*A61B 34/30* (2016.01)
*A61B 90/11* (2016.01)

(52) U.S. Cl.
CPC .............. *A61B 34/30* (2016.02); *A61B 90/11* (2016.02)

(58) Field of Classification Search
CPC .............. A61B 34/30; A61B 2034/301; A61B 2034/302; A61B 2034/303;
(Continued)

(56) References Cited

U.S. PATENT DOCUMENTS

2008/0091101 A1* 4/2008 Velusamy .......... A61B 10/0233
600/427

FOREIGN PATENT DOCUMENTS

| CN | 102723296 A | 10/2012 |
| CN | 103919626 A | 7/2014 |

(Continued)

*Primary Examiner* — Samuel S Hanna
(74) *Attorney, Agent, or Firm* — Cheng-Ju Chiang

(57) ABSTRACT

The invention relates to an orthopedic surgical device and an orthopedic surgery robot system. Wherein, the orthopedic surgical device includes an orthopedic surgical tool and two movable mechanisms, the two movable mechanisms respectively provide the orthopedic surgical tool with reciprocating motion variables in different directions; the orthopedic surgical device also includes a decoupling mechanism and a clamping mechanism; the clamping mechanism installs the orthopedic surgical tool and is connected to the decoupling mechanism; the decoupling mechanism is connected to two movable mechanisms, and the two movable mechanisms enable the orthopedic surgical tool to reach any position within a motion range. The invention makes the operation simpler and easier, has higher stability, higher accuracy, and improves operation efficiency, reduces the doctor's labor load and uncontrollable risks of the surgery during manual operation, and increases the controllability and safety of the surgery.

9 Claims, 11 Drawing Sheets

(58) Field of Classification Search
CPC ........ A61B 2034/304; A61B 2034/305; A61B 2034/306
See application file for complete search history.

(56) References Cited

FOREIGN PATENT DOCUMENTS

| | | |
|---|---|---|
| CN | 106272364 A | 1/2017 |
| CN | 108206155 A | 6/2018 |
| TW | 286505 B | 9/2007 |
| WO | 2009/103743 A1 | 8/2009 |

* cited by examiner

ORTHOPEDIC SURGICAL DEVICE AND ORTHOPEDIC SURGICAL ROBOT SYSTEM

CROSS REFERENCE TO RELATED APPLICATIONS

The present invention is a 35 U.S.C. § 371 National Phase conversion of International (PCT) Patent Application No. PCT/CN2021/104851, filed on Jul. 6, 2021, which claims benefit of Chinese Application No. 202010642040.1, filed on Jul. 6, 2020, the disclosure of which is incorporated by reference herein. The PCT International Patent Application was filed in Chinese.

FIELD OF THE INVENTION

The present invention relates to the field of medical devices, particularly to a device and a robot system for use in orthopedic surgery that can be used for grinding, bone cutting or other operating functions in orthopedic surgery.

BACKGROUND OF THE INVENTION

In orthopedic surgery, the accuracy and stability of surgical control are very important. The key to the success of osteotomy is whether the positioning without damaging the human nerve tissue can be accurately performed in accordance with the preoperative planning to achieve the purpose of surgical treatment.

There is still no intelligent automatic osteotomy tool directly applied to orthopedic surgical robots. In most cases, the doctor still uses the existing orthopedic electric grinder or ultrasonic osteotomy, and the doctor performs the osteotomy using these tools by his hands. The amount of grinding or the cutting of the ultrasonic osteotomy is not well controlled, and it is easy to cause nerve damage. Some orthopedic surgical robots are equipped with osteotomy tools on a tool-mounting end of the robotic arm. The follow-up method is adopted during the operation, and the binocular visual navigation system is still required for the doctor to hold the osteotomy tool for operation, so that the osteotomy tool can be tightly held. The orthopedic surgical robot is used to hold the osteotomy tool, which can increase the stability of the osteotomy tool in space, but it still requires the doctor to manually control the tool, and it needs to be controlled by the doctor in real time according to the prompts of the navigation system. The orthopedic surgical robot is not intelligent enough, and the doctor needs pay close attention to the prompts of the navigation system, and the workload of the doctor is not low.

Therefore, there is a need to provide an osteotomy device that is convenient and simple to operate, has high accuracy, high stability, can improve surgical efficiency, and reduce surgical injuries, and an intelligent automatic osteotomy system that can avoid the difficulty and risk of manual operation.

TECHNICAL PROBLEM

A main object of the present invention is to provide an orthopedic surgical device that is convenient and simple to operate, has high accuracy, high stability, and can improve surgical efficiency.

Another object of the present invention is to provide an orthopedic surgical robot system that is convenient and simple to operate, has high accuracy, high stability, and can improve surgical efficiency.

TECHNICAL SOLUTION

In order to achieve the purposes of the present invention, the following technical solutions are provided:

an orthopedic surgical device, comprising an orthopedic surgical tool and two movable mechanisms, the two movable mechanisms respectively provide the orthopedic surgical tool with reciprocating motion variables in different directions; the orthopedic surgical device further comprises a decoupling mechanism a clamper; the clamper is used to hold the orthopedic surgical tool and is connected to the decoupling mechanism; the decoupling mechanism is connected to the two movable mechanisms, the orthopedic surgical tool can reach any position within a motion range by means of the two movable mechanisms.

In some embodiments, one of or both the movable mechanisms comprise a base, a linear motor and a movable platform installed on the base; the linear motor comprises stator and mover; the mover is connected to a corresponding movable platform, and capable of driving the movable platform to perform a reciprocating motion; and the movable platform is connected to the decoupling mechanism, and capable of taking the decoupling mechanism to perform a corresponding reciprocating motion.

In some embodiments, the two movable mechanisms are installed on the same base; the linear motors of the two movable mechanisms are installed at different positions on the same base; the base is an integral structure; and the base is T-shaped, L-shaped or cross-shaped.

In some embodiments, the movable mechanism further comprises a linear guide or a cross-roller guide installed on the base; the mover of the linear motor drives the movable platform to slide along the linear guide or the cross-roller guide; the linear guide is provided with a sliding block; the mover of the linear motor is connected to the sliding block; the movable mechanism further comprises a limit switch and limit blocks; the limit switch is installed on the base, and the limit blocks are arranged at both ends of each movable platform and cooperates with the corresponding limit switch for limiting a motion range of the corresponding movable platform; the movable mechanism further comprises a grating ruler and a reading head, the grating ruler is arranged along a motion route of the corresponding movable platform, the position information is obtained by the reading head, and the grating ruler and the reading head cooperate with each other to detect the position of the corresponding movable platform.

In some embodiments, the two movable mechanisms are selected from: a horizontal movable mechanism, a depth movable mechanism, and a vertical movable mechanism; the horizontal movable mechanism provides a horizontal reciprocating motion variable; the depth movable mechanism provides a reciprocating motion variable in the depth direction; and the vertical movable mechanism provides vertical reciprocating motion variable.

In some embodiments, the decoupling mechanism comprises a mounting seat and a decoupling connecting seat; the mounting seat and the decoupling connecting seat are connected in a relatively movable manner; the clamper is installed to the mounting seat; the mounting seat and the decoupling connecting seat are respectively connected to the movable platforms of the two movable mechanisms; the decoupling mechanism is capable of driving the clamper to take the orthopedic surgical tool to a predetermined position within a motion range thereof by means of the two movable mechanisms.

In some embodiments, the decoupling mechanism further comprises a decoupling guide rail; the decoupling guide rail is installed on the mounting seat, and is provided with a sliding block; the decoupling connecting seat is connected to the sliding block, and capable of sliding without dispatching off relative to the decoupling guide rail by means of the sliding block; the mounting seat is relatively movably or fixedly connected with the movable platform of one movable mechanism, and the decoupling connecting seat is relatively movably or fixedly connected with the movable platform of the other movable mechanism.

In some embodiments, the mounting seat is relatively slidably connected with the movable platform of one movable mechanism, a front side of the movable platform of the one movable mechanism is provided with the linear guide or the cross-roller guide; the mounting seat is installed to the front side of the movable platform, and can perform a reciprocating motion on the front side of the movable platform along the linear guide or the cross-roller guide; a back side of the movable platform is connected to the mover of the linear motor of the movable mechanism; and the decoupling connecting seat is fixedly connected with the movable platform of the other movable mechanism.

In some embodiments, the clamper comprises a tool clamp, a tool clamp seat and a sensor; the tool clamp seat and the tool clamp are fixed together for clamping the orthopedic surgical tool therebetween; the sensor is installed between the mounting seat of the decoupling mechanism and the tool clamp seat, and used to detect force and torque of various directions during the orthopedic surgical tool work.

In some embodiments, the tool clamp and the tool clamp seat are connected by guide posts; the sensor is a six-axes sensor, which is connected to the surgical robot or a control center; the base of the movable mechanisms is provided with an interface seat for flange connection with an arm of the surgical robot.

Another orthopedic surgical device provided in the present invention, comprises: an orthopedic surgical tool and multiple movable mechanisms, the multiple movable mechanisms respectively provide the orthopedic surgical tool with reciprocating motion variables in different directions, at least one of the multiple movable mechanisms comprises a movable platform, a linear motor, a linear guide or a cross-roller guide; the linear motor comprises stator and mover; the movable platform is connected to the mover, and is capable of performing a reciprocating motion along the stator under a drive of the mover; the linear guide or cross-roller guide is used to guide the reciprocating motion of the movable platform.

Further, the at least one movable mechanism is a horizontal movable mechanism, a depth movable mechanism, or a vertical movable mechanism; the horizontal movable mechanism provides a reciprocating motion variable in the horizontal direction; the depth movable mechanism provides a reciprocating motion variable in the depth direction; the vertical movable mechanism provides a reciprocating motion variable in the vertical direction; the at least one movable mechanism comprises a base; the movable mechanism further comprises a limit switch and limit blocks; the limit switch is installed on the base, and the limit blocks are arranged at both ends of each movable platform and cooperates with the corresponding limit switch for limiting a motion range of the movable platform; the movable mechanism further comprises a grating ruler and a reading head, the grating ruler is arranged along a moving route of the movable platform, the reading head is used for reading position information, and the grating ruler and the reading head cooperate with each other to detect the position of the corresponding movable platform.

In some embodiments, each movable mechanism comprises a base, a movable platform and a drive element installed on the base, and the drive element is used for driving the movable platform to move linearly and reciprocally relative to the base; the movable platforms and/or the bases of each movable mechanism are connected with each other; the orthopedic surgical tool is capable of reaching any position within a motion range by means of the multiple movable mechanisms; the orthopedic surgical tool is connected to the movable mechanism of one movable mechanism.

In some embodiments, the orthopedic surgical device comprises a clamper; the orthopedic surgical tool is installed in the clamper; the clamper comprises a tool clamp, a tool clamp seat, and a sensor; the tool clamp seat and the tool clamp are fixed together for clamping the orthopedic surgical tool therebetween; the tool clamp seat is connected to the movable platform of the one movable mechanism; the sensor is installed on the tool clamp seat, and is used to detect force and torque of the orthopedic surgical tool in various directions during working.

An orthopedic surgical robot system provided in the present invention, comprises a surgical robot, an orthopedic surgical tool, and the orthopedic surgical device as described above for installing the orthopedic surgical tool; and the orthopedic surgical device is connected to the surgical robot.

Further, the orthopedic surgical robot comprises a control center of the system, the movable mechanism of the orthopedic surgical device comprises a drive motor, and the drive motor is connected to the control center; the orthopedic surgical device is provided with a sensor that is connected to the control center, the orthopedic surgical tool is provided with a navigation surface recognizable by a vision system, the orthopedic surgical robot system further comprises a binocular vision system, the binocular vision system is capable of recognizing the navigation surface; the orthopedic surgery device is provided with an interface seat, which is flange-connected with an arm of the surgical robot.

In some embodiments, the orthopedic surgical device includes an orthopedic surgical tool and at least two movable mechanisms that are connected in sequence, and the at least two movable mechanisms respectively provide the orthopedic surgical tool with linear reciprocating motion variables in different directions. The axes of the at least two movable mechanisms along are perpendicular to each other.

In some embodiments, the present invention adopts a mechanical movable mechanism that can improve control precision, accuracy, and stability to achieve linear reciprocating motion variables in different directions, and the reciprocating motion variables provided by the at least two movable mechanisms are perpendicular to each other, so as to obtain the automatic movement control of orthopedic surgery tools in at least two directions, which makes the operation simpler and easier, higher stability, higher precision, and improved surgical efficiency. The controllable motion variables provided by the movable mechanisms, reduces the doctor's labor and uncontrollable risks during manual operation, and increases the controllability and safety of the surgery.

In some embodiments, the orthopedic surgical device includes three movable mechanisms, the orthopedic surgical tool and the three movable mechanisms are sequentially connected, and the three movable mechanisms provide the orthopedic surgical tool reciprocating motion variables in different directions, and the three movable mechanisms are perpendicular to each other along their respective axes in different directions.

In some embodiments, each of the movable mechanisms includes a driving motor, a slider rail, and a movable platform, and the movable platform can make linear reciprocating motion along the slider rail under the drive of the driving motor. The surgical tool and the at least two movable mechanisms are sequentially connected in a connection manner that: the orthopedic surgical tool is installed on the movable platform of one of the movable mechanisms, and the movable mechanisms are respectively installed in sequence to the movable platform of another adjacent movable mechanism.

It is possible to realize that the movable platform can reciprocate linearly along the slide rail under the drive of the drive motor. There may be many different implementations. In some embodiments, cross-roller guides are installed between the movable platform and the slide rail.

In some embodiments, the movable mechanism further includes a screw assembly, the screw assembly includes a ball screw arranged along the slide rail, and a screw nut engaged with the ball screw; the movable platform is fixed on the screw nut, and the drive motor is connected to and drives the ball screw, so that a relative linear reciprocating motion can be obtained between the movable platform and the ball screw.

In some embodiments, a rotatable clamping mechanism is further provided between the orthopedic surgical tool and the connected movable mechanism, and the rotatable clamping mechanism is installed on the movable mechanism connected to the orthopedic surgical tool. The orthopedic surgical tool is connected to the rotatable clamping mechanism. In some embodiments, the rotatable clamping mechanism includes a driving motor and a gear set connected to the output of the driving motor, and the gear set output is connected to the orthopedic surgical tool.

In some embodiments, the orthopedic surgical tool includes an electric grinder or an ultrasonic osteotome.

In some embodiments, the orthopedic surgical device is also provided with a camera for real-time close monitoring the surgical site.

The present invention also provides an orthopedic surgical robot system, which includes the orthopedic surgical device as described above, and a control center; and the movable mechanism of the orthopedic surgical device includes a drive motor. The drive motor is connected with the control center.

In some embodiments, the orthopedic surgical device is provided with a sensor, the sensor is connected to the control center, the orthopedic surgical tool is provided with a navigation surface that can be recognized by a vision system, and the orthopedic surgical robot system further includes a binocular vision system, which can recognize the navigation surface.

In some specific embodiments, the sensor is a six-axes sensor, which is installed to the movable mechanism.

ADVANTAGES

Compared with the prior art, the present invention has the following advantages:

the present invention realizes linear reciprocating motion variables in different directions by means of mechanical movable mechanisms that can improve control precision, accuracy and stability. The linear reciprocating motion variables provided by at least two movable mechanisms are perpendicular to each other, so as to automatically control the orthopedic surgical tool moving in at least two directions, thereby make the operation easier, more stable, higher precision, and improved operation efficiency. The controllable motion variables provided by the movable mechanism reduce doctors' labor load and the uncontrollable risks of surgery during manual operation, and have increased the controllability and safety of surgery.

The present invention can be used for orthopedic surgery robots, and can obtain automatic grinding, bone cutting and other functions in orthopedic surgery when used together with an orthopedic surgery robot.

DETAILED DESCRIPTION OF THE INVENTION

Figure 1:
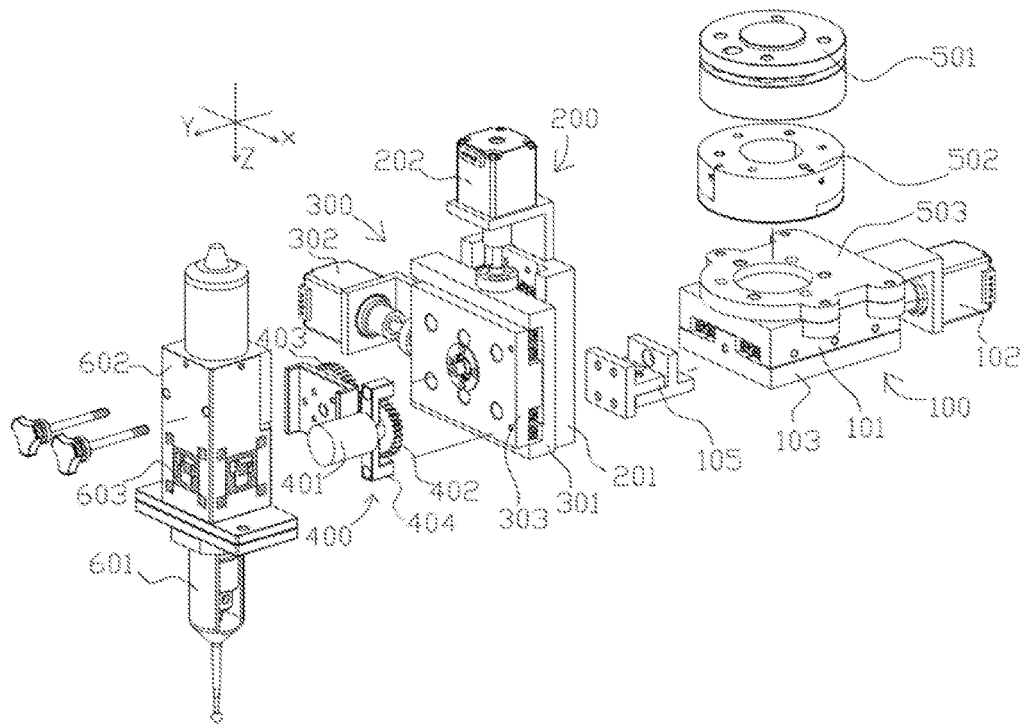
FIG. 1 is an exploded view of an orthopedic surgical device in accordance with a first embodiment of the present invention.

The following will clearly and completely describe the technical solutions in the embodiments of the present invention. Obviously, the described embodiments are only a part of the embodiments of the present invention, rather than all the embodiments. Based on the embodiments of the present invention, all other embodiments obtained by those of ordinary skill in the art without creative work shall fall within the protection scope of the present invention.

It is worth noting that the direction terms mentioned in the present invention, for example, "horizontal", "vertical", "depth direction", "upper", "lower", "front", "rear", "left", "right", "inner", "outer", "side", etc., are only the directions with reference to the attached drawings. Therefore, the directional terms used are for a better and clearer description and understanding of the present invention. It does not indicate or imply that the device or components must have a specific orientation, be constructed or operated in a specific orientation, and therefore cannot be understood as a limitation of the present invention.

In order to explain the present invention in more detail, embodiments of the orthopedic surgical device provided by the present invention will be described in detail below with reference to the accompanying drawings.

The orthopedic surgical device in accordance with the first, second, and fourth embodiments of the present invention comprises an orthopedic surgical tool and three movable mechanisms. The orthopedic surgical tool and the three movable mechanisms are connected in sequence, and the three movable mechanisms respectively provide the orthopedic surgical tool with reciprocating moveable variables in different directions, and the three movable mechanisms are perpendicular to each other along their respective axes in different directions. The connection of the orthopedic surgical tool and the three movable mechanisms is as follows: the orthopedic surgical tool is installed on a movable platform of one of the movable mechanisms, and the three movable mechanisms are respectively installed on a movable platform of another adjacent movable mechanism in sequence. The orthopedic surgical device in the third embodiment comprises an orthopedic surgical tool and two movable mechanisms. The two movable mechanisms respectively provide the orthopedic surgical tool with reciprocating moveable variables in different directions, and the two movable mechanisms are perpendicular to each other along their respective axes in different directions. The orthopedic surgical tool and the two movable mechanisms are sequentially connected in a manner that the orthopedic surgical tool is installed on a movable platform of one of the movable mechanisms, and the movable mechanism connected with the orthopedic surgical tool is installed on a movable platform of the other movable mechanism. In the third embodiment, a camera for real-time close monitoring the surgical site is used. The fifth embodiment is an alternative embodiment based on the first embodiment, specifically, the orthopedic surgical tool in the first embodiment is replaced to an ultrasonic osteotome.

In FIGS. 1, 3, 4, 6, 7, 9, 10, 12, the right-handed or Cartesian coordinate system in engineering is used, which defines according to the figures: the positive direction of the X-axis is to the right; the positive direction of the Y-axis is forward; the positive direction of the Z-axis is downward; X represents the horizontal direction, Y represents the vertical direction, and Z represents the depth direction. The definition of the front, back, left, right, up, and down of the coordinate axis just correspond to the directions of the figures. The direction terms used here are for a better and clearer description and understanding of the present invention, rather than indicating or implying that the device or component must have the specific orientation, be constructed or operated in the specific orientation. Therefore, it cannot be understood as a limitation of the present invention.

Figure 2:
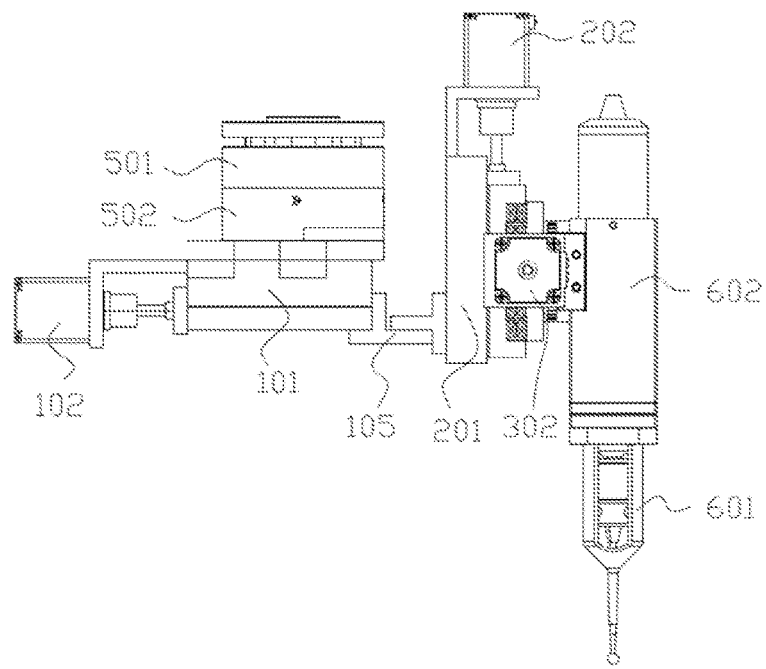
FIG. 2 is a side view of the orthopedic surgical device in accordance with the first embodiment of the present invention.
Figure 3:
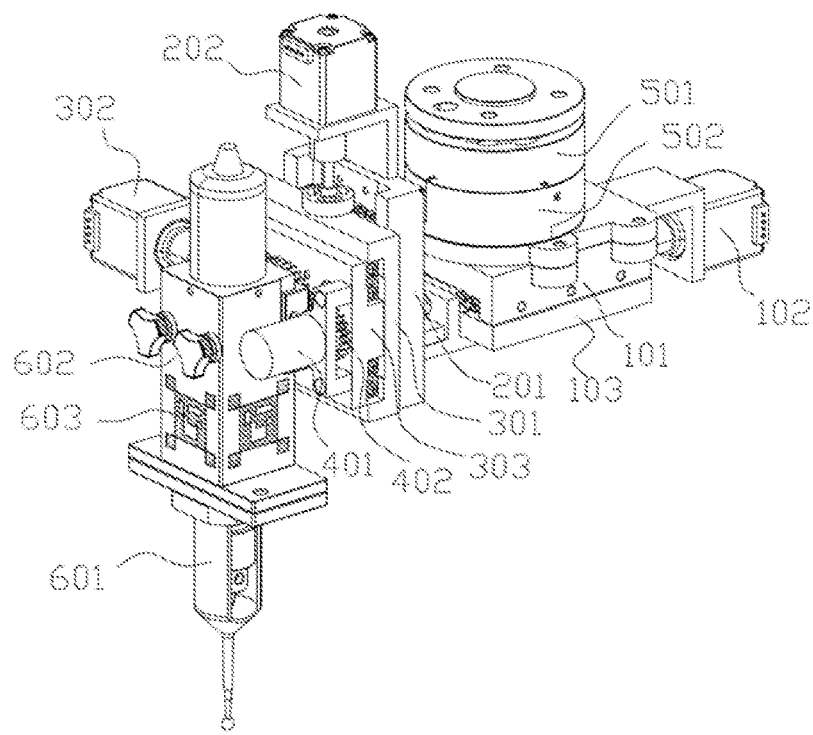
FIG. 3 is a perspective view of the orthopedic surgical device in accordance with the first embodiment of the present invention.

Please refer to FIGS. 1 to 3. In the first embodiment, the three movable mechanisms are a vertical movable mechanism 100, a horizontal movable mechanism 300 and a depth movable mechanism 200, respectively, which provide reciprocating motion variables along the vertical, horizontal, and depth directions. In the coordinate axis of FIG. 1, X represents the horizontal direction, Y represents the vertical direction, and Z represents the depth direction. The superposition of reciprocating motion variables in the three directions of vertical, horizontal, and depth directions allows the orthopedic surgical tool to reach any position within a certain space range, thereby, the convenient, simple, high-precision, and stable surgical operation can be obtained using the orthopedic surgical tool, the efficiency of surgery can be improved, and the risk of surgery can be reduced.

The vertical movable mechanism 100 comprises a vertical drive motor 102, a mounting seat 101 mounted with a vertical slide rail, and a vertical movable platform 103. The vertical movable platform 103 can be reciprocated along the mounting seat 101 under the drive of the vertical drive motor 102. The vertical slide rail mounted on the mounting seat 101 is a cross-roller guide (not shown) in this embodiment. A connecting platform 503 and an installation interface seat 501 are installed on the mounting seat 101. Through the installation interface seat 501, the orthopedic surgical device can be installed to a surgical robot. The position and depth of grinding and cutting can be precisely controlled according to the preoperative planning, which can reduce the deviation caused by manual operation and ensures the accuracy of the operation.

The orthopedic surgical device is also provided with a six-axes sensor 502, which can accurately measure the forces and torque in various directions during the osteotomy process, detect the motion variables in various dimensions, avoid surgical accidents, and improve control accuracy.

The depth movable mechanism 200 comprises a depth drive motor 202, a mounting seat 201 installed with a depth slide rail, and a depth movable platform. The depth movable platform can be linearly reciprocated along the mounting seat 201 under the drive of the depth drive motor 202. The depth slide rail mounted on the mounting seat 201 adopts a cross-roller guide (not shown) in this embodiment. The mounting seat 201 is installed on the vertical movable platform 103. Specifically, a detachable installation is obtained between the mounting seat 201 and the vertical movable platform 103 through a quick release seat 105. As an embodiment, the quick release seat 105 can be fixed to the mounting seat 201 and the vertical movable platform 103 by screws (thumb screws), respectively, and is respectively tightly fitted with the mounting seat 201 and the vertical movable platform 103.

The horizontal movable mechanism 300 comprises a horizontal drive motor 302, a mounting seat 301 installed with a horizontal slide rail, and a horizontal movable platform 303. The horizontal movable platform 303 can be linearly reciprocated along the mounting seat 301 under the drive of the horizontal drive motor 302, and the horizontal slide rail mounted on the mounting seat 301 is a cross-roller guide (not shown) in this embodiment. The mounting seat 301 directly serves as the depth movable platform of the depth movable mechanism, is installed on the mounting seat 201, and is connected to and driven by the depth drive motor 202.

Further, each drive motor can be connected by a coupling for driving.

In the embodiment, the orthopedic surgical tool is installed on the horizontal movable platform 303 of the horizontal movable mechanism, and a rotatable clamper 400 in the depth direction is also provided between the orthopedic surgical tool and the connected horizontal movable platform 303. The rotatable clamper 400 is installed on the horizontal movable platform 303 connected to an orthopedic surgical tool, and the orthopedic surgical tool is connected to the rotatable clamper 400. The rotatable clamper 400 comprises a rotating drive motor 401, a mounting seat 404, a driving gear 402 and a driven gear 403 that mesh with each other. The driving motor is connected to and drives the driving gear 402, and an output of the driven gear 403 is coupled with the orthopedic surgical tool. Furthermore, the rotatable clamper 400 is provided with hand-tightening quick-release screws, which can quickly clamp the orthopedic surgical tool.

The orthopedic surgical tool comprises an electric grinder 601 driven by an orthopedic electric drill and a mounting seat 602, and the mounting seat 602 is connected to the rotatable clamper 400. The mounting seat 602 is provided with a navigation surface 603, which can be recognized by a vision system for real-time tracking. The orthopedic surgical tool in other embodiments may also be an ultrasonic osteotome.

Figure 16:
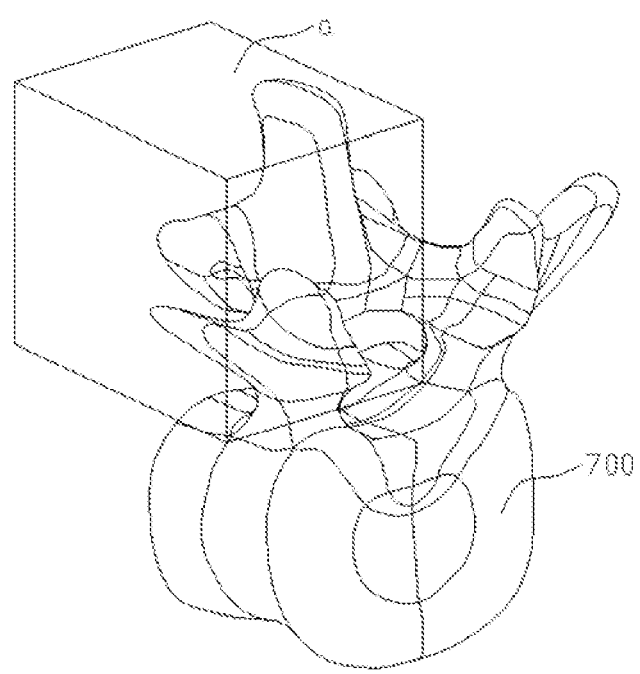
FIG. 16 illustrates one working space of the orthopedic surgical device of the present invention.
Figure 17:
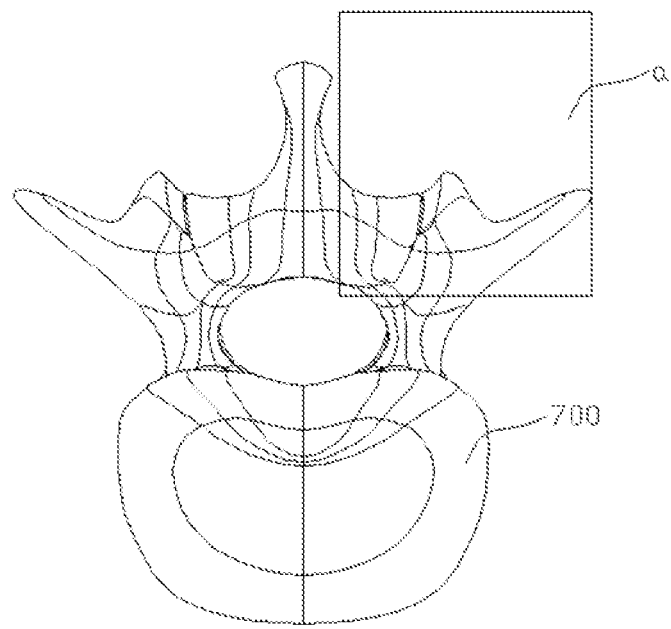
FIG. 17 illustrates another working space of the orthopedic surgical device of the present invention.
Figure 18:
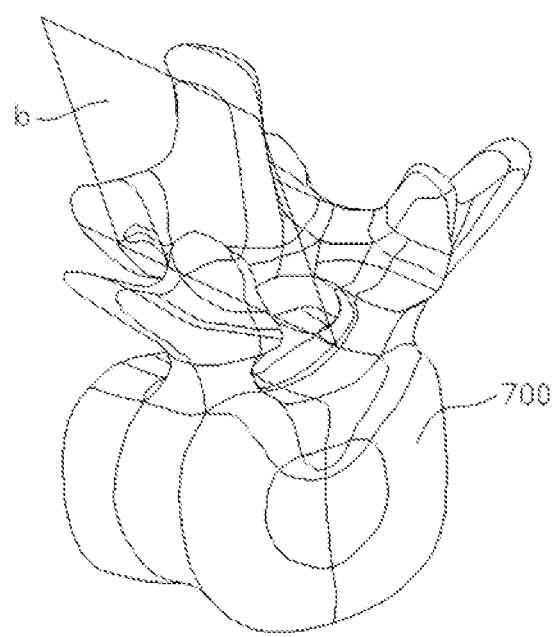
FIG. 18 illustrates one working plan of the orthopedic surgical device of the present invention.
Figure 19:
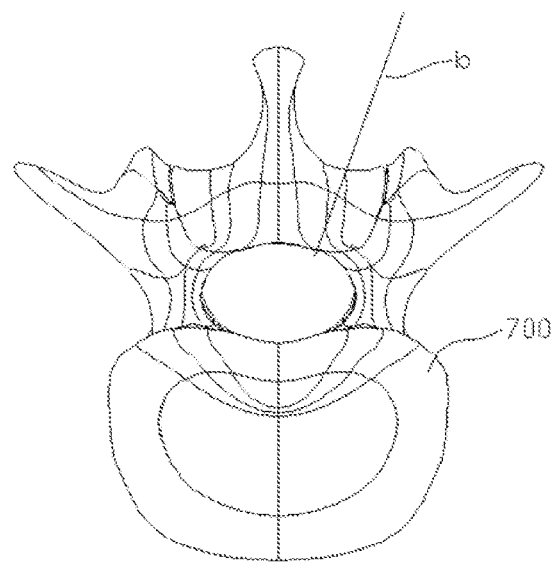
FIG. 19 illustrates another working plan of the orthopedic surgical device of the present invention.

Please refer to FIGS. 16-19, using the orthopedic surgical device of the present invention, the orthopedic surgical tool can be linearly reciprocated in three directions: vertical, horizontal, and depth, and motion variables in the three directions cam be superimposed, so that the orthopedic surgical tool can reach any position within a certain space range. For the spine 700 to be operated on as shown in FIGS. 16 and 17, when using the orthopedic surgical device of the present invention, the orthopedic surgical tool can move at any position in the three-dimensional space "a" of the surgical site of the spine 700 to be operated on; or, according to need, can move at any position in the plane "b" of the surgical site of the spine 700 to be operated on as shown in FIGS. 18 and 19. Thereby the orthopedic surgical tool can realize the convenient, simple, high-precision, and stable surgical operation, the efficiency of surgery can be improved, and the risk of surgery can be reduced.

Figure 4:
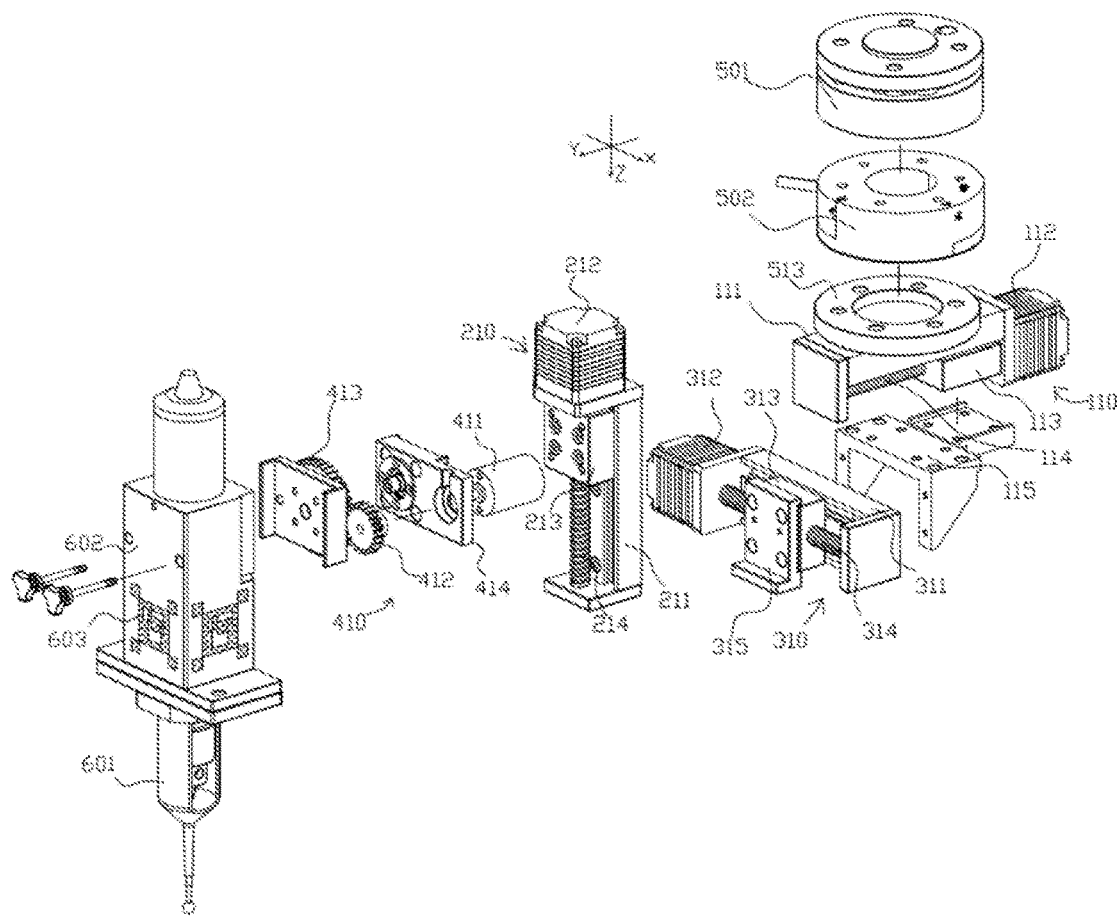
FIG. 4 is an exploded view of the orthopedic surgical device in accordance with a second embodiment of the present invention.
Figure 5:
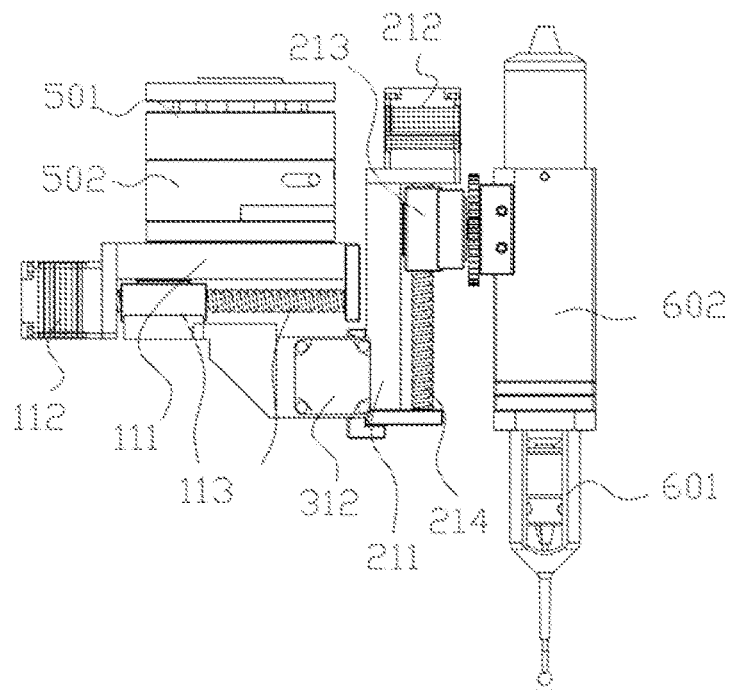
FIG. 5 is a side view of the orthopedic surgical device in accordance with the second embodiment of the present invention.
Figure 6:
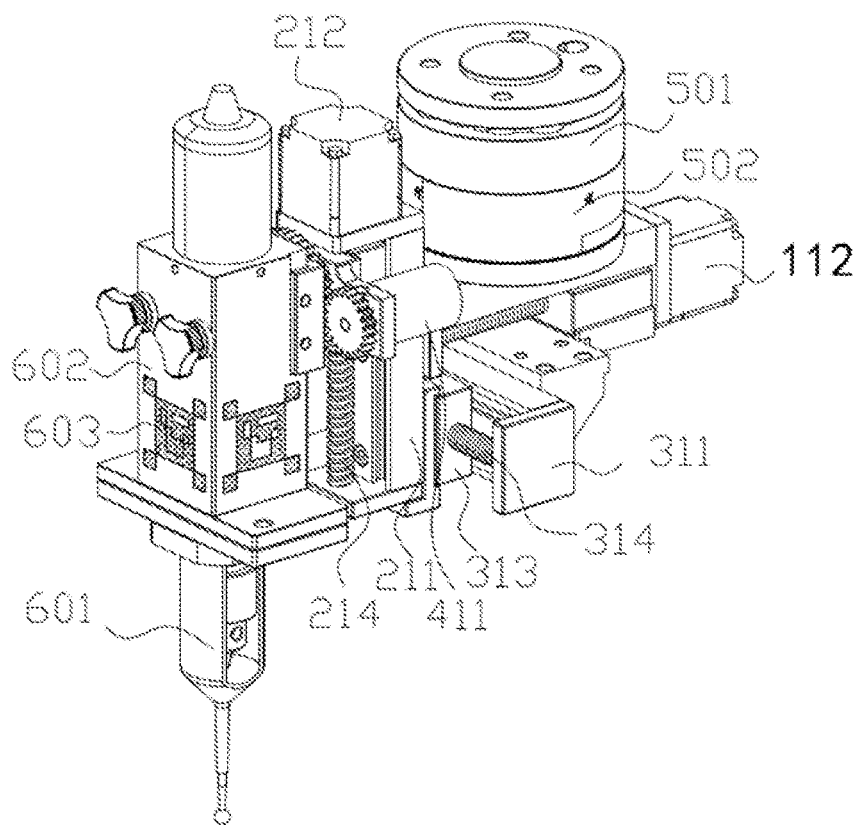
FIG. 6 is a perspective view of the orthopedic surgical device in accordance with the second embodiment of the present invention.

Please refer to FIGS. 4-6, in the second embodiment, the three movable mechanisms are the vertical movable mechanism 110, the horizontal movable mechanism 310 and the depth movable mechanism 210, respectively, which provide reciprocating motion variables along the vertical, horizontal, and depth directions respectively. In the coordinate axis of FIG. 4, X corresponds to the horizontal direction, Y corresponds to the vertical direction, and Z corresponds to the depth direction. The superposition of reciprocating motion variables in the three directions of vertical, horizontal and depth allows the orthopedic surgical tool to reach any position within a certain space range. Thereby the orthopedic surgical tool can realize the convenient, simple, high-precision, and stable surgical operation, the efficiency of surgery can be improved, and the risk of surgery can be reduced.

The vertical movable mechanism 110 comprises a vertical drive motor 112, a mounting seat 111 mounted with a vertical slide rail, and a vertical movable platform 115. The vertical movable mechanism 110 comprises a vertical screw assembly. The vertical screw assembly comprises a vertical ball screw 114 arranged along the vertical slide rail, and a screw nut 113 coupled with the vertical ball screw 114. The vertical movable platform 115 is fixed on the screw nut 113. The vertical drive motor 112 is connected to and drives the vertical ball screw 114, so that a relative linear reciprocating motion can be obtained between the vertical movable platform 115 and the vertical ball screw 114.

A connecting platform 513 and an installation interface seat 501 are installed on the mounting seat 111. Through the installation interface seat 501, the orthopedic surgical device can be installed to a surgical robot. The position and depth of grinding and cutting can be precisely controlled according to the preoperative planning, which reduces the deviation caused by manual operation and ensures the accuracy of the operation. The orthopedic surgical device is also provided with a six-axes sensor 502, which can accurately detect the forces and torque in various directions during the osteotomy process, detect motion variables in various dimensions, avoid surgical accidents, and improve control accuracy.

The horizontal movable mechanism 310 comprises a horizontal drive motor 312, a mounting seat 311 installed with a horizontal slide rail, and a horizontal movable platform 315. The horizontal movable mechanism 310 also comprises a horizontal screw assembly. The horizontal screw assembly comprises a horizontal ball screw 314 arranged along the horizontal slide rail, and a screw nut 313 coupled with the ball screw 314. The horizontal movable platform 315 is fixed on the screw nut 313. The driving motor 312 is connected to and drives the horizontal ball screw 314, so that a relative reciprocating motion can be obtained between the horizontal movable platform 315 and the horizontal ball screw 314. The mounting seat 311 is installed on the vertical movable platform 115.

The depth movable mechanism 210 comprises a depth drive motor 212, a mounting seat 211 installed with a depth slide rail, and a depth movable platform 213. The depth movable mechanism 210 also comprises a depth screw assembly, which comprises a deep ball screw 214 arranged along the deep slide rail, the depth movable platform 213 is provided with internal threads that are coupled with the deep ball screw 214, and the depth driving motor 212 is connected to and drives the deep ball screw 214, so that a relative reciprocating motion can be obtained between the depth movable platform 213 and the depth ball screw 214. The mounting seat 211 is installed on the horizontal movable platform 315.

Further, each drive motor can be connected by a coupling for driving.

In the embodiment, the orthopedic surgical tool is installed on the depth movable platform 213 of the depth movable mechanism 210, and a rotatable clamper 410 is also provided between the orthopedic surgical tool and the connected depth movable platform 213. The rotatable clamper 410 is installed on the depth movable platform 213 connected with an orthopedic surgical tool, and the orthopedic surgical tool is connected to the rotatable clamper 410. The rotatable clamper 410 comprises a rotating drive motor 411, a mounting seat 414, a driving gear 412 and a driven gear 413 that are engaged with each other. The driving motor is connected to and drives the driving gear 412, and the output of the driven gear 413 is connected to the orthopedic surgical tool. Furthermore, the rotatable clamper 410 is provided with hand-tightening quick-release screws, which can quickly clamp orthopedic surgical tools.

The orthopedic surgical tool comprises an electric grinder 601 driven by an orthopedic electric drill and a mounting seat 602, and the mounting seat 602 is connected to the rotatable clamper 410. The mounting seat 602 is provided with a navigation surface 603, which can be recognized by a vision system for real-time tracking. The orthopedic surgical tool in other embodiments may also be an ultrasonic osteotome.

Figure 7:
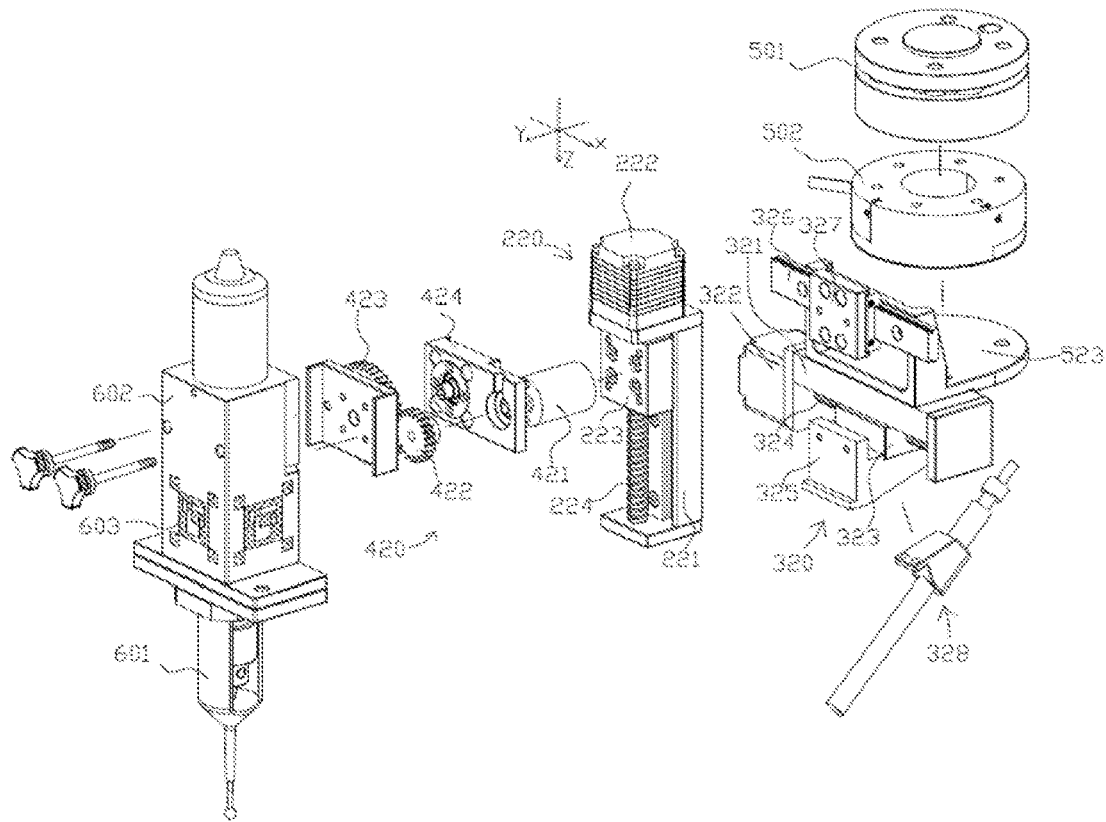
FIG. 7 is an exploded view of the orthopedic surgical device in accordance with a third embodiment of the present invention.
Figure 8:
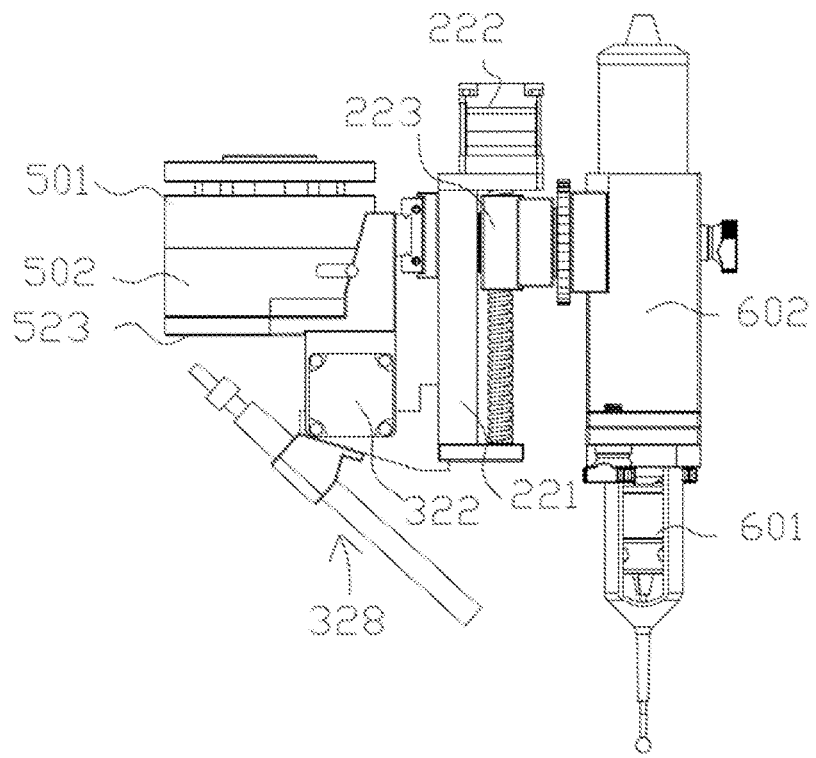
FIG. 8 is a side view of the orthopedic surgical device in accordance with the third embodiment of the present invention.
Figure 9:
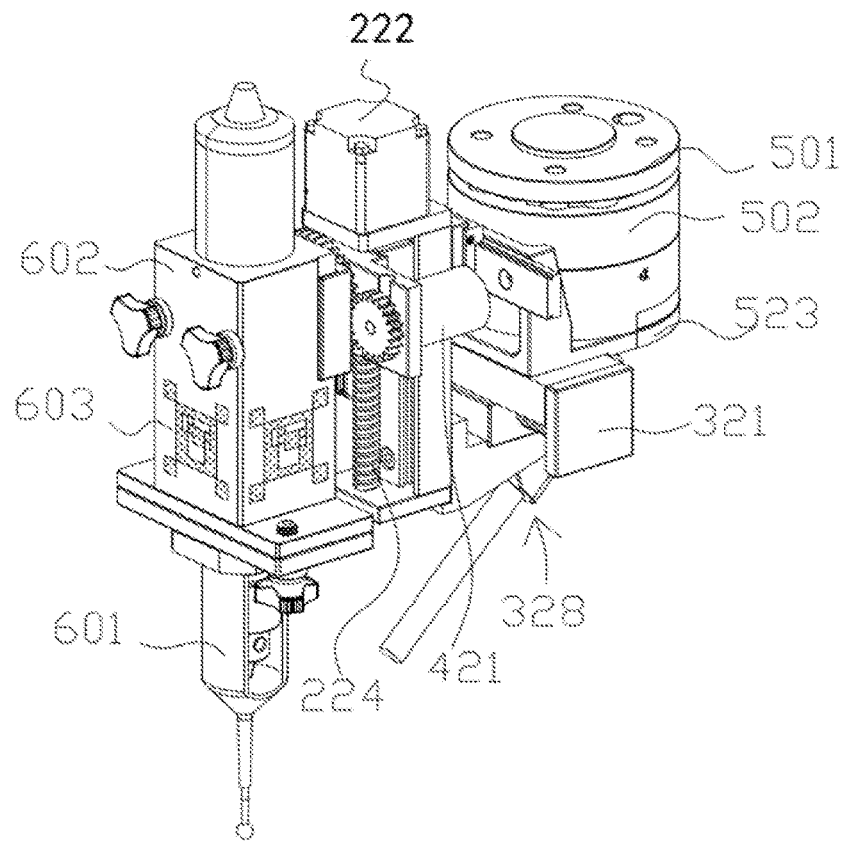
FIG. 9 is a perspective view of the orthopedic surgical device in accordance with the third embodiment of the present invention.

Please refer to FIGS. 7-9, the difference from the first and second embodiments is that the orthopedic surgical device described in the third embodiment comprises an orthopedic surgical tool and two movable mechanisms connected in sequence, and the two movable mechanisms are respectively provider the orthopedic surgical tools with reciprocating motion variables in different directions, and the axes of the two movable mechanisms along are perpendicular to each other.

In the third embodiment, the two movable mechanisms are the horizontal movable mechanism 320 and the depth movable mechanism 220, respectively, which provide reciprocating motion variables in the horizontal direction and the depth direction, respectively. In the coordinate axis of FIG. 7, X represents the horizontal direction, Y represents the vertical direction, and Z represents the depth direction. The superposition of the reciprocating motion variables in the horizontal and depth directions can allow the orthopedic surgical tool to reach any position within a certain plane range, so as to realize the convenient, simple, high-precision, and stable surgical operation of the orthopedic surgical tool, the efficiency of surgery can be improved and the risk of surgery can be reduced.

The horizontal movable mechanism 320 comprises a horizontal drive motor 322, a mounting seat 321 installed with a horizontal slide rail, and a horizontal movable platform 325. The horizontal movable mechanism 320 also comprises a horizontal screw assembly, which comprises a horizontal ball screw 324 arranged along the horizontal slide rail, and a screw nut 323 coupled with the ball screw 324, the horizontal movable platform 325 is fixed on the screw nut 323, the horizontal driving motor 322 is connected to and drives the horizontal ball screw 324, so that a relative reciprocating motion can be obtained between the horizontal movable platform 325 and the horizontal ball screw 324.

A connecting platform 523 and an installation interface seat 501 are installed on the horizontal movable mechanism 320. Through the installation interface seat 501, the orthopedic surgical device can be installed to a surgical robot. The position and depth of the grinding and cutting can be accurately controlled according to the preoperative planning, which can reduce the deviation caused by manual operation and ensure the accuracy of the operation. The orthopedic surgical device is also provided with a six-axes sensor 502, which can accurately detect the forces and torque in various directions during the osteotomy process, detect motion variables in various dimensions, avoid surgical accidents, and improve control accuracy.

The depth movable mechanism 220 comprises a depth drive motor 222, a mounting seat 221 installed with a depth slide rail, and a depth movable platform 223. The depth movable mechanism 220 also comprises a depth screw assembly that comprises a ball screw 224 is arranged along the depth slide rail. The depth movable platform 223 is provided with internal threads that are engaged with the depth ball screw 224, and the depth driving motor 222 is connected to and drives the depth ball screw 224, so that a relative reciprocating motion can be obtained between the depth movable platform 223 and the depth ball screw 224. One end of the mounting seat 221 is installed on the horizontal movable platform 325, and the other end is connected to a sliding block 327 fixed on a guide rail 326 on the connecting platform 523. This structure can improve the rigidity of the depth movable mechanism 220.

Further, each drive motor can be connected by a coupling for driving.

In the embodiment, the orthopedic surgical tool is installed on the depth movable platform 223 of the depth movable mechanism 220, and a rotatable clamper 420 is also provided between the orthopedic surgical tool and the connected depth movable platform 223. The rotatable clamper 420 is installed on the depth movable platform 223 connected with an orthopedic surgical tool, and the orthopedic surgical tool is connected to the rotatable clamper 420. The rotatable clamper 420 comprises a rotating driving motor 421, a mounting seat 424, a driving gear 422 and a driven gear 423 that are engaged with each other. The driving motor is connected to and drives the driving gear 422, and the output of the driven gear 423 is connected to the orthopedic surgical tool. Further, the rotatable clamper 420 is provided with hand-tightening quick-release screws, which can quickly clamp orthopedic surgical tools.

The orthopedic surgical tool comprises an electric grinder 601 driven by an orthopedic electric drill and a mounting seat 602, and the mounting seat 602 is connected to the rotatable clamper 420. The mounting seat 602 is provided with a navigation surface 603, which can be recognized by a vision system for real-time tracking. The orthopedic surgical tool in other embodiments may be an osteotomy tool or an ultrasonic osteotome, or other surgical tools.

In addition, a camera 328 is fixed on the horizontal movable platform 325 for real-time close monitoring of the operation site during the operation.

Figure 10:
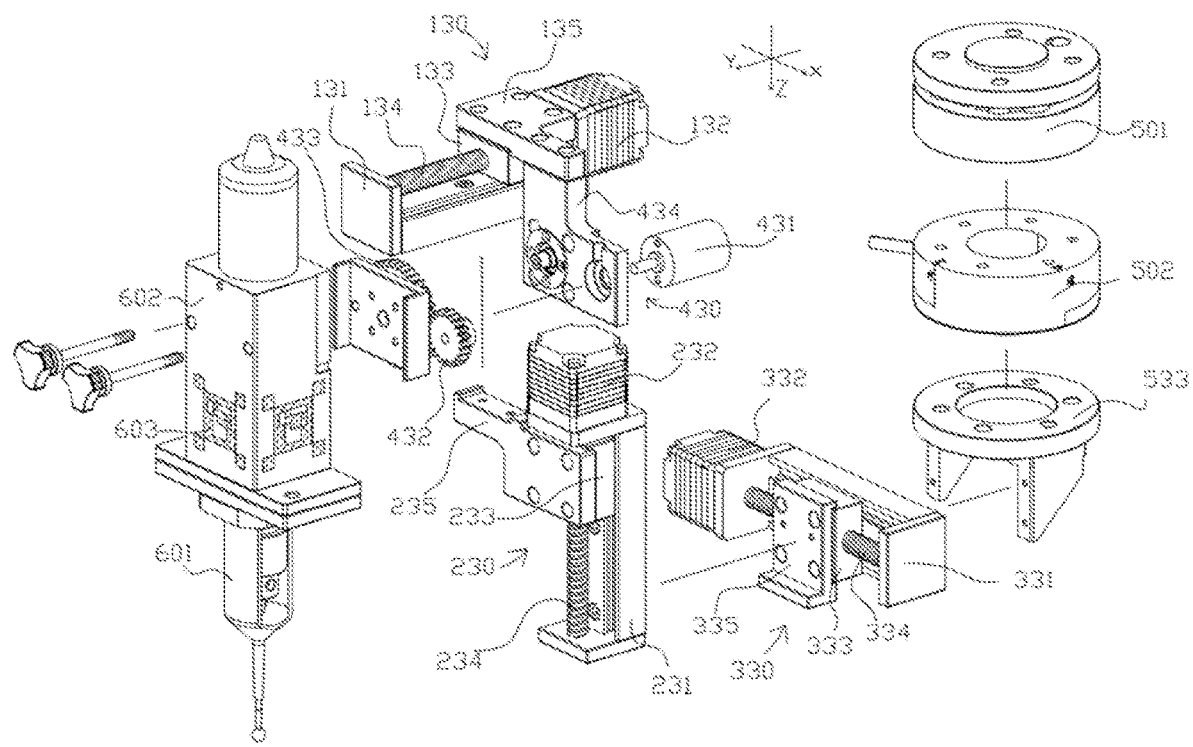
FIG. 10 is an exploded view of the orthopedic surgical device in accordance with a fourth embodiment of the present invention.
Figure 11:
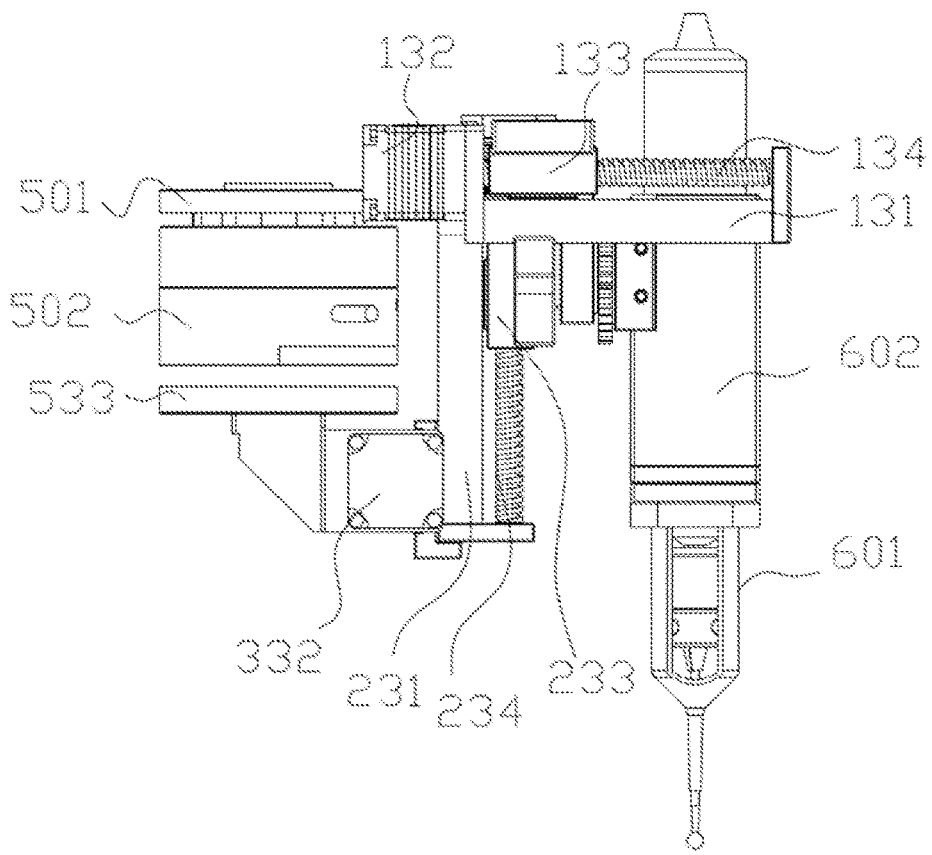
FIG. 11 is a side view of the orthopedic surgical device in accordance with the fourth embodiment of the present invention.
Figure 12:
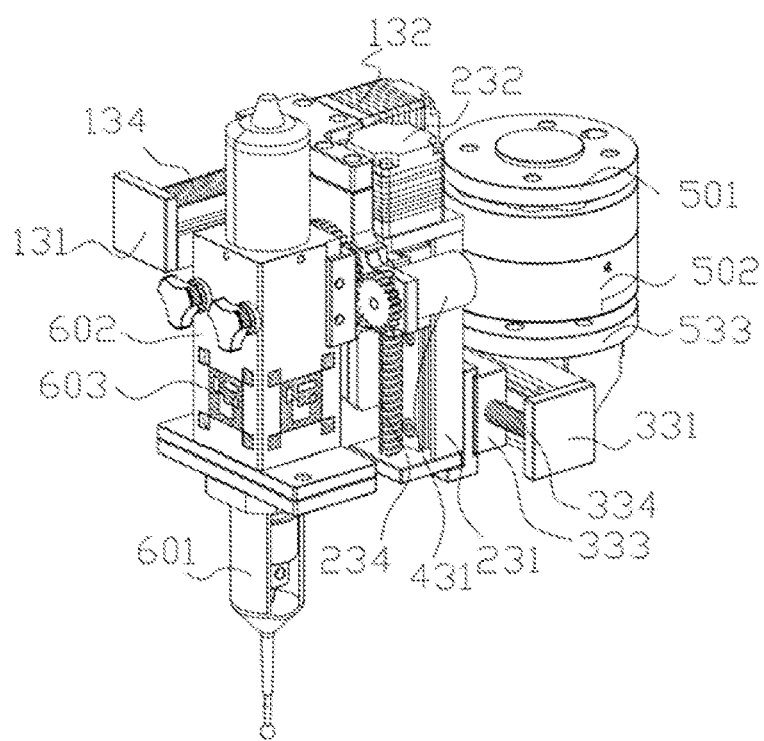
FIG. 12 is a perspective view of the orthopedic surgical device in accordance with the fourth embodiment of the present invention.

Please refer to FIGS. 10-12. In the fourth embodiment, the three movable mechanisms are the vertical movable mechanism 130, the horizontal movable mechanism 330 and the depth movable mechanism 230, respectively, which provide reciprocating motion variables along the vertical, horizontal, and depth directions. In the coordinate axis of FIG. 10, X represents the horizontal direction, Y represents the vertical direction, and Z represents the depth direction. The superposition of reciprocating motion variables in the three directions of vertical, horizontal and depth allows the orthopedic surgical tool to reach any position within a certain space range, thereby the convenient, simple, high-precision, and stable surgical operation of the orthopedic surgical tool can be obtained. The efficiency of surgery can be improved and the risk of surgery can be reduced.

The horizontal movable mechanism 330 comprises a horizontal drive motor 332, a mounting seat 331 installed with a horizontal slide rail, and a horizontal movable platform 335. The horizontal movable mechanism 330 also comprises a horizontal screw assembly, which comprises a horizontal ball screw 334 arranged along the horizontal slide rail, and a screw nut 333 coupled with the ball screw 334.

The horizontal movable platform 335 is fixed on the screw nut 333, and the horizontal driving motor 332 is connected to and drives the horizontal ball screw 334, so that a relative reciprocating motion can be obtained between the horizontal movable platform 335 and the horizontal ball screw 334.

A connecting platform 533 and an installation interface seat 501 are installed on the horizontal movable mechanism 330. Through the installation interface seat 501, the orthopedic surgical device can be installed to a surgical robot. The position and depth of the grinding and cutting can be accurately controlled according to the preoperative planning, which can reduce the deviation caused by manual operation and ensure the accuracy of the operation. The orthopedic surgical device is also provided with a six-axes sensor 502, which can accurately detect the forces and torque in various directions during the osteotomy process, detect motion variables in various dimensions, avoid surgical accidents, and improve control accuracy.

The depth movable mechanism 230 comprises a depth drive motor 232, a mounting seat 231 installed with a depth slide rail, and a depth movable platform 235. The depth movable mechanism 230 also comprises a screw assembly, which comprises a depth ball screw 234 arranged along the depth slide rail and a screw nut 233 engaged with the depth ball screw 234, the depth movable platform 235 is fixed on the depth screw nut 233, and the depth driving motor 232 is connected to and drives the deep ball screw 234 so that a relative reciprocating motion can be obtained between the deep movable platform 235 and the deep ball screw 234. The mounting seat 231 is installed on the horizontal movable platform 335.

The vertical movable mechanism 130 comprises a vertical drive motor 132, a mounting seat 131 mounted with a vertical slide rail, and a vertical movable platform 135. The vertical movable mechanism 130 comprises a vertical screw assembly, which comprises a vertical ball screw 134 arranged along the vertical slide rail, and a screw nut 133 engaged with the vertical ball screw 134. The vertical movable platform 135 is fixed to the screw nut 133, the vertical drive motor 132 is connected to and drives the vertical ball screw 134, so that a relative reciprocating motion can be obtained between the vertical movable platform 135 and the vertical ball screw 134. The mounting seat 131 is installed on the depth movable platform 235. Specifically, the depth movable platform 235 has a horizontal shoulder (not labeled) extending laterally, and the mounting seat 131 is installed to the horizontal shoulder of the depth movable platform 235.

Further, each drive motor can be connected by a coupling for driving.

In the embodiment, the orthopedic surgical tool is installed on the vertical movable platform 135 of the vertical movable mechanism 130, and a rotatable clamper 430 is provided between the orthopedic surgical tool and the connected vertical movable platform 135. The rotatable clamper 430 is installed on the vertical movable platform 135 connected with an orthopedic surgical tool, and the orthopedic surgical tool is connected to the rotatable clamping mechanism clamper 430. The rotatable clamper 430 comprises a rotating drive motor 431, a mounting seat 434, a driving gear 432 and a driven gear 433 that mesh with each other. The driving motor is connected to and drives the driving gear 432, and the output of the driven gear 433 is connected to the orthopedic surgical tool. Further, the rotatable clamper 430 is provided with hand-tightening quick-release screws, which can quickly clamp orthopedic surgical tools.

The orthopedic surgical tool comprises an electric grinder 601 driven by an orthopedic electric drill and a mounting seat 602, and the mounting seat 602 is connected to the rotatable clamper 430. The mounting seat 602 is provided with a navigation surface 603, which can be recognized by a vision system for real-time tracking. The orthopedic surgical tool in other embodiments may be an ultrasonic osteotome.

Figure 13:
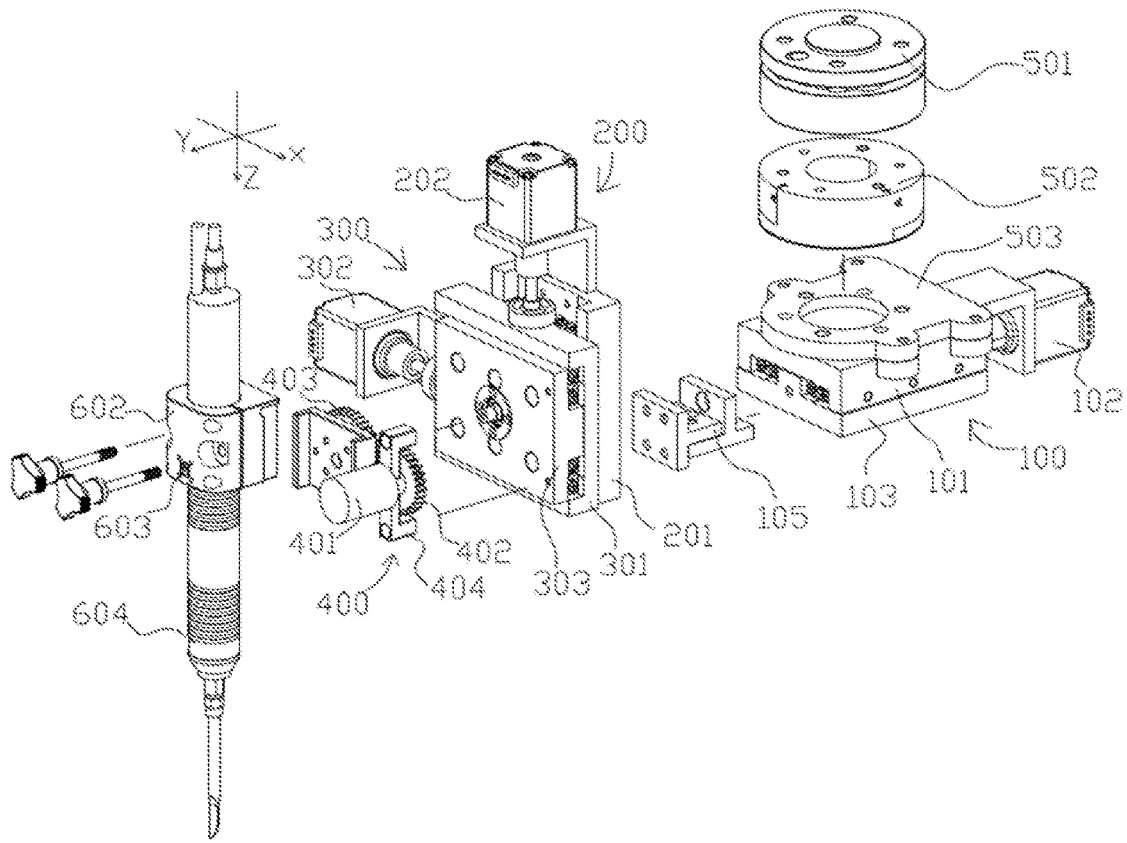
FIG. 13 is an exploded view of the orthopedic surgical device in accordance with a fifth embodiment of the present invention.
Figure 14:
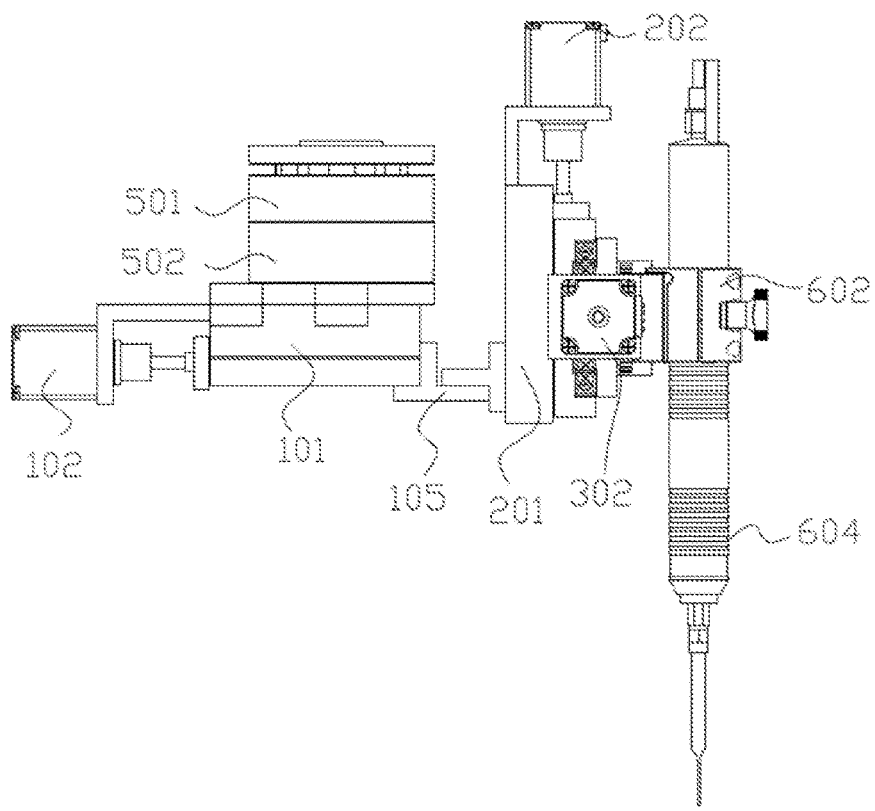
FIG. 14 is a side view of the orthopedic surgical device in accordance with the fifth embodiment of the present invention.
Figure 15:
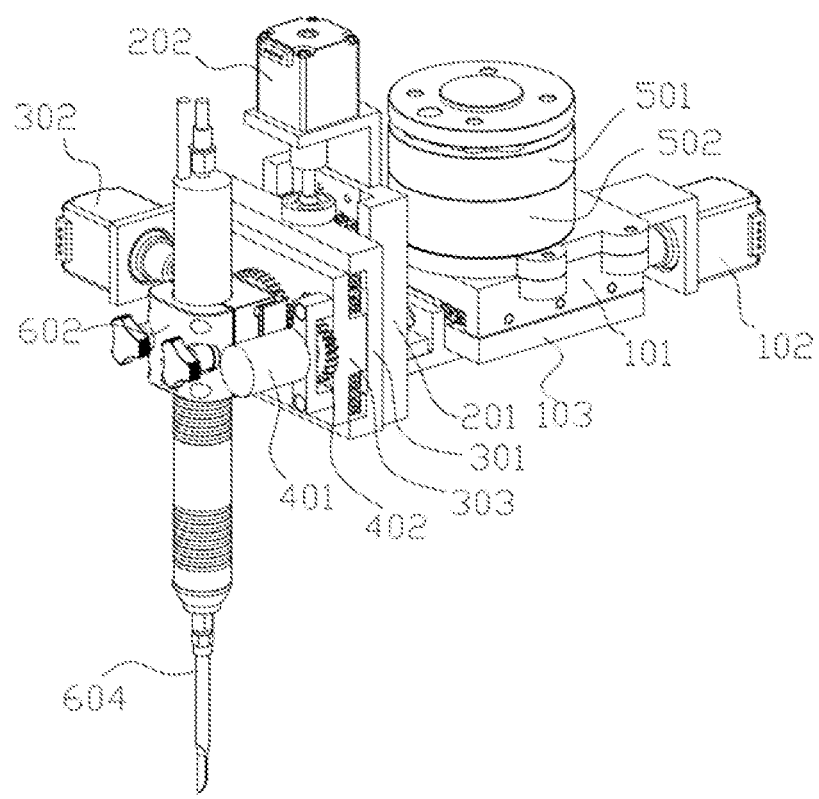
FIG. 15 is a perspective view of the orthopedic surgical device in accordance with the fifth embodiment of the present invention.

As shown in FIGS. 13 to 15, the fifth embodiment is different from the first embodiment in that the orthopedic surgical tool used is an ultrasonic osteotome 604.

As alternative embodiments, the at least two movable mechanisms of the orthopedic surgical device may comprise a horizontal movable mechanism and a vertical movable mechanism, or, may comprise a vertical movable mechanism and a depth movable mechanism.

The present invention also provides an orthopedic surgical robot system, which comprises the orthopedic surgical device in any of the above-mentioned embodiments and a surgical robot. The orthopedic surgical device is used to install the surgical tool to the surgical robot through the installation interface seat 501. The orthopedic surgical robot system comprises a control center, and each movable mechanism of the orthopedic surgical device comprises a drive motor electrically connected to the control center. The control center can be set in the surgical robot or set in a controlling table out of the orthopedic surgical robot for function control and data processing. The orthopedic surgical device can use a six-axes sensor, which is installed to the movable mechanism and is electrically and communicatively connected with the control center. The orthopedic surgical tool is provided with a navigation surface 603 that can be recognized by the vision system. The orthopedic surgical robot system comprises a binocular vision system, which can recognize the navigation surface. The binocular vision system can be installed to the orthopedic surgical device, or be placed next to the operating bed by a bracket, or fixed above the operating bed by a support. The control center has a control circuit electrically connected and communicated with a computer through RSS485 or CAN bus, so as to perform the predetermined grinding operation or cutting operation according to preoperative planning. The orthopedic surgical robot system of the present invention can automatically perform the osteotomy operation using the tool, without the operation of the doctor, and the doctor can only focus on monitoring the entire process, which can reduce the labor intensity of the doctor.

Figure 20:
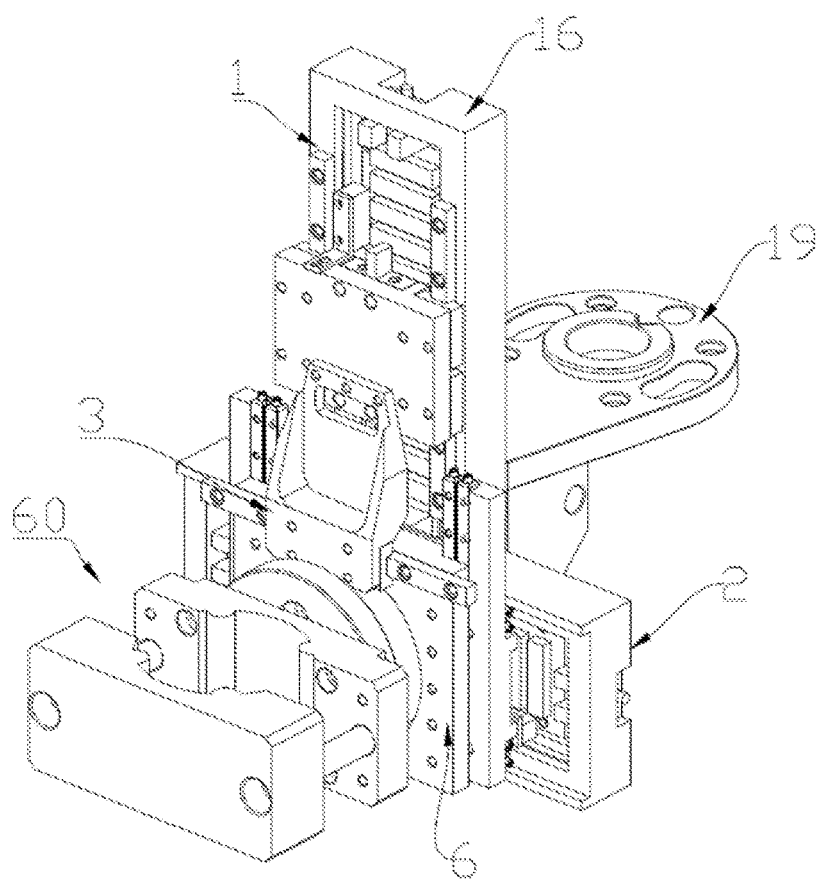
FIG. 20 is a perspective view of an orthopedic surgical device in accordance with a sixth embodiment of the present invention.
Figure 21:
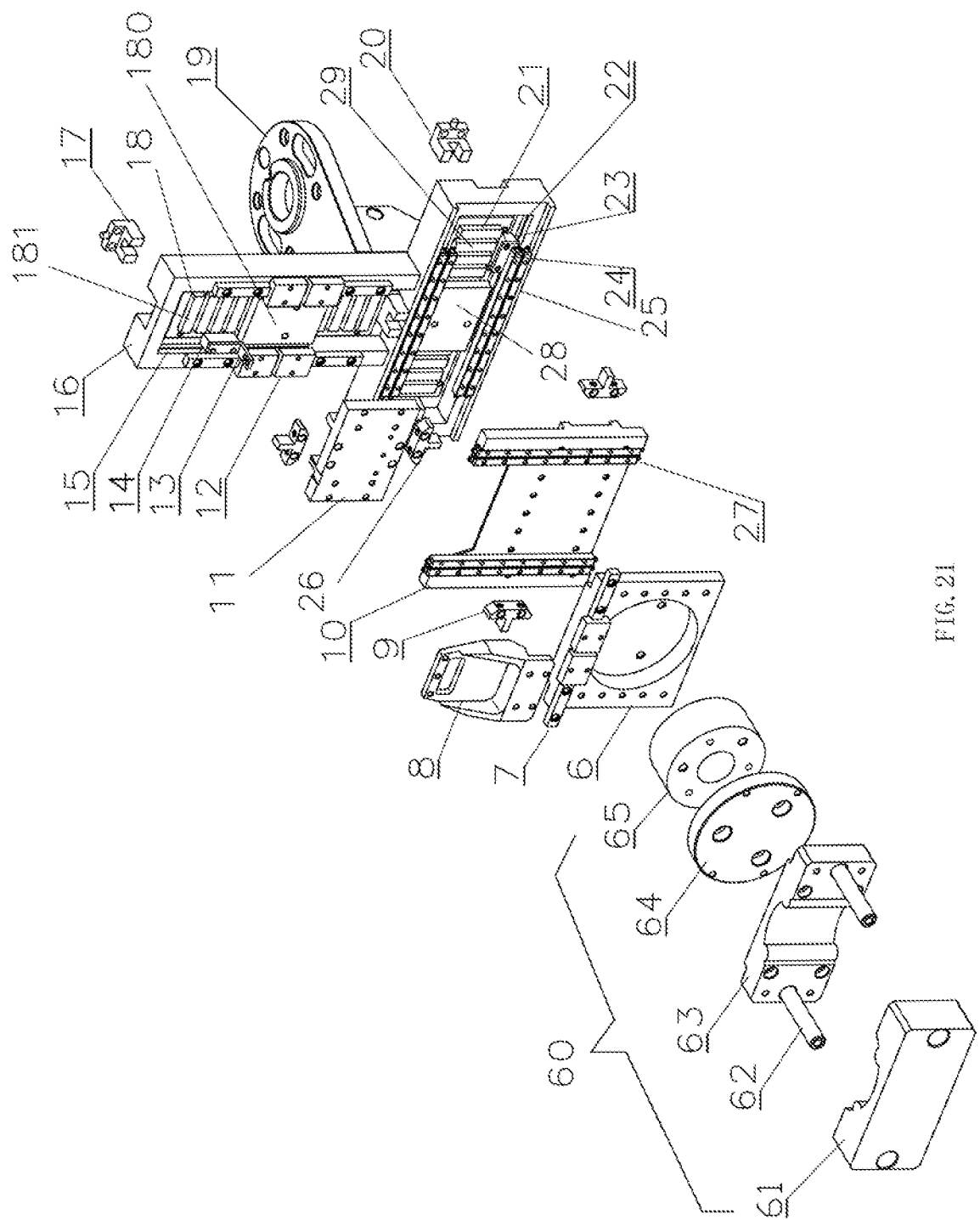
FIG. 21 is an exploded view of the orthopedic surgical device in accordance with the sixth embodiment of the present invention.

Referring to FIGS. 20-21, the orthopedic surgical device in accordance with the sixth embodiment of the present invention, comprises a base 16, and a depth movable mechanism 1 and a horizontal movable mechanism 2 mounted on the base 16, and further comprises a decoupling mechanism 3 and a surgical tool clamper 60. An orthopedic surgical tool (not shown) can be installed to the surgical tool clamper 60.

The orthopedic surgical tool may be a drill, an ultrasonic bone knife or other surgical tools. The depth movable mechanism 1 and the horizontal movable mechanism 2 respectively provide reciprocating motion variables in the horizontal and depth directions, so that the decoupling mechanism 3 of this embodiment can move in both the horizontal and depth directions.

The horizontal movable mechanism 2 of the orthopedic surgical device comprises a linear motor 21 mounted on the base 16, the horizontal slide rail including a pair of cross-roller guides 25, a horizontal grating ruler 22, a horizontal reading head 23, a mounting seat 24 for installing the horizontal reading head, a horizontal limit switch 20, and horizontal limit blocks 9 mounting at both ends of a horizontal movable platform 10. A mover 28 of the linear motor 21 is installed on the horizontal movable platform 10 and drives the horizontal movable platform 10 to make a reciprocating motion along the cross-roller guides 25. Stator 29 of the linear motor 21 is set between a pair of cross-roller guides 25. In this embodiment, the linear motor is a flat-plate linear motor or a U-slot linear motor. The horizontal limit switch 20 is installed to the base 16, which can be located at opposite ends of the stator 29 or the cross-roller guides 25. Both ends of the horizontal movable platform 10 are provided with horizontal limit blocks 9 to limit end positions of the reciprocating motion of the horizontal movable platform 10 respectively, and cooperate with the horizontal limit switch 20 to determine whether the horizontal movable platform 10 moves to the end position. The horizontal limit switch 20 can be a position sensor, which can detect the position of the horizontal movable platform 10, and further control switching the linear motor 21 based on the detection of the limit switch.

The depth movable mechanism of the orthopedic surgical device comprises a linear motor 18 installed on the base 16, a linear guide 12, a depth grating ruler 15, a depth reading head 14, a mounting seat 13 for mounting the depth reading head, a depth limit switch 17, and a depth limit block 26 mounted to a depth movable platform 11. A mover 180 of the linear motor 18 is installed to the depth movable platform 11 and drives the depth movable platform 11 to make a reciprocating motion along the linear guide 12. Stator 181 of the linear motor 18 is set between a pair of linear guides 12, the linear guide 12 is provided with a sliding block, and the mover 180 is connected to the sliding block to form a slidable fit with the linear guide 12. The depth limit switch 17 is installed to the base 16 and can be located at the end of the stator 181 or the end of the linear guide 12, horizontal limit blocks 26 can be set at opposite ends of the depth limit switch 17 to respectively limit the two end positions of the reciprocating motion of the depth movable platform 11, and cooperate each other to detect whether the depth movable platform 11 moves to the limit position at the end. The depth limit switch 17 can be a position sensor, and the linear motor 18 can be further controlled to switch through the detection of the limit switch.

The grating rulers 22, 15 are mounted on the base 16, and are arranged at one side of the stator of the linear motor, or at one side of any of the cross-roller guides 25 or the linear guide 12. The reading heads 23, 14 are installed on the movable platforms 10, 11 through the reading head mounting seats 24, 13 and are arranged at one side of the stator of the linear motor, or at one side of any of the cross-roller guides 25 or linear guide 12, and are used to determine the moving position of the mover or the movable platform. The grating ruler 22 and the horizontal reading head 23 can be replaced by other position sensors in the prior art.

In this embodiment, the horizontal movable mechanism and the depth movable mechanism are arranged on the same base 16 (T-shaped or cross-shaped). The base 16 may comprise two flat plates to form a T-shape or a cross-shape, or may be a one-piece plate (unseparated, such as a casting) of a T-shape or a cross-shape. The interface seat 19 is mounted to the base 16. In this implementation, the linear motors 18, 21 and the movable platforms are arranged on the front side of the base 16, and the interface seat 19 is arranged on the back side of the base 16 for connecting with the surgical robot. The horizontal movable mechanism and the depth movable mechanism are arranged on the same base 16, and the linear motor is engaged with the linear guide or cross-roller guide, which can avoid a necessary of multiple bases, multiple rotating motors, or multiple transmission mechanism; and directly obtain linear movement by the driving element. Therefore, the orthopedic surgical device of the present invention has higher structural accuracy, better rigidity, and more convenient manufacturing and assembly.

The decoupling machine 3 comprises a mounting seat 6, a decoupling guide rail 7, a decoupling connecting seat 8, and the vertical slide rail including cross-roller guides 27 installed on the horizontal movable platform 10. A pair of cross-roller guides 27 are provided on the horizontal movable platform 10, and perpendicular to the decoupling guide rail 7. The pair of cross-roller guides 27 and the decoupling guide rail 7 respectively guide the decoupling mechanism to move linearly in the horizontal and depth directions. In this embodiment, the decoupling guide rail 7 is a horizontal linear guide, and a pair of cross-roller guides 27 are arranged along the depth direction. The decoupling guide rail 7 is fixed on the mounting seat 6, and is provided with a sliding block thereon. The sliding block can slide along the guide rail 7 without detaching away. One end of the decoupling connecting seat 8 is fixed on the depth movable platform 11, and the other end is fixed on the sliding block of the decoupling guide rail 7. The decoupling connecting seat 8 can be taken to slide horizontally along the guide rail 7 by means of the sliding block, and the sliding block does not slide off the guide rail 7. Therefore, the decoupling mechanism is connected to the base 16 by means of fixing the decoupling connecting seat 8 to the depth movable platform 11. The mounting seat 6 is used to install the surgical tool clamper 60. The decoupling guide rail 7 is fixedly connected to the mounting seat 6. The mounting seat 6 can move linearly along the cross-roller guides 27 set on the horizontal movable platform 10, specifically along the depth direction. In this embodiment, the mounting seat 6 has a flat structure, the front side (one side) is used to install the surgical tool clamper 60, and the back side is slidably fitted with the cross-roller guides 27 on the horizontal movable platform 10. The decoupling mechanism can reach any position in the plane travel range under the cooperation of the depth and horizontal movable mechanisms. Specifically, the horizontal movable platform 10 can move horizontally to drive the mounting seat 6 (so as to drive the surgical tool clamper 60) to move horizontally and linearly, at this time, the decoupling guide rail 7 moves horizontally and linearly; and the decoupling guide rail 7 and the decoupling connecting seat 8 slide relatively through the sliding block. One end of the decoupling connecting seat 8 is fixed to the depth movable platform 11, and no movement occurs in the horizontal direction. The depth movable platform 11 drives the mounting seat 6 (thus drive the surgical tool clamper 60) to move linearly in the depth direction as a whole through the decoupling connecting seat 8, and the mounting seat 6 moves linearly in the depth direction along the cross-roller guides 27.

The surgical tool clamper 60 comprises a tool clamp 61, a tool clamp seat 63, guide posts 62, a sensor interface base 64 and a six-axes sensor 65. The tool clamp 61 and the tool clamp seat 63 are connected through the guide posts 62 and clamp the surgical tool therebetween. The tool clamp seat 63, the sensor interface base 64 and the six-axes sensor 65 are sequentially installed on the mounting seat 6 of the decoupling mechanism. The surgical tool clamper can clamp a drill or an ultrasonic osteotome, or clamp other orthopedic surgical tools. The six-axes sensor 5 can accurately measure forces and torque in various directions during orthopedic surgery, detect motion variables in various dimensions, avoid surgical accidents, and improve control accuracy.

Different from other embodiments, the drive elements of this embodiment are mounted on a plane instead of superimposed, so that the orthopedic surgical device can obtain advantages of compact structure, excellent rigidity and stability.

The orthopedic surgical device is connected to a flange of an arm end of the orthopedic surgical robot through the interface seat 19 to form the orthopedic surgical robot system of the present invention. The orthopedic surgical robot has a control center. The linear motors, sensors, and switches of the orthopedic surgical device, are electrically and communicatively connected to the control center, and are controlled by the control center. The control center can also be set in a controlling table out of the surgical robot and the orthopedic surgical device; while the surgical robot has a control PCB, which is electrically connected and/or communicatively connected with the motors and sensors of the orthopedic surgical device, and is electrically and communicatively connected with the control center for functional control and data information processing. The orthopedic surgical device is provided with a navigation surface that can be recognized by the vision system, and the orthopedic surgical device or the surgical robot further comprises a binocular vision system, which can recognize the navigation surface.

The structures in the above embodiments can be combined or replaced with each other.

In other embodiments, the orthopedic surgical device of the present invention may be provided with two or more movable mechanisms, and multiple movable mechanisms respectively provide the orthopedic surgical tool with reciprocating motion variables in different directions. At least one of the multiple movable mechanisms comprises a movable platform, a linear motor, a linear guide, or a cross-roller guide. The linear motor comprises stator and a mover. The movable platform is connected to the mover and is driven to perform reciprocating motion along the stator; the linear guide or the cross-roller guide is used for guiding the reciprocating motion of the movable platform.

The foregoing are only preferred embodiments of the present invention, and the protection scope of the present invention is not limited thereto. Any equivalent transformation based on the technical solution of the present invention shall fall within the protection scope of the present invention.

What is claimed is:

1. An orthopedic surgical device for operating an orthopedic surgical tool, comprising:
    two movable mechanisms respectively providing the orthopedic surgical tool with reciprocating motion variables in different directions from a horizontal direction, a depth direction, and a vertical direction;
    a decoupling mechanism; and
    a clamper for clamping the orthopedic surgical tool;
    wherein each of the two movable mechanisms comprises: a base, and a linear motor, a movable platform and a linear guide or a cross-roller guide, all of which are mounted on the base; the linear motor comprises a stator and a mover; the mover drives a corresponding movable platform to slide along the linear guide or the cross-roller guide, where the linear guide is provided with a sliding block, and the mover is connected to the sliding block; the mover is connected to the corresponding movable platform for driving the movable platform to perform a reciprocating motion; the corresponding movable platform is connected with the decoupling mechanism for taking the decoupling mechanism to perform a corresponding reciprocating motion together;
    the decoupling mechanism comprises: a mounting seat and a decoupling connecting seat connected with the mounting seat in a relatively movable manner;
    the clamper is installed to the mounting seat to hold the orthopedic surgical tool to the decoupling mechanism;
    the mounting seat and the decoupling connecting seat are respectively connected to the respective movable platforms of the two movable mechanisms, whereby one movable mechanism drives the decoupling mechanism moving by means that the corresponding movable platform takes the mounting seat of the decoupling mechanism to perform a corresponding reciprocating motion together, and the other movable mechanism drives the decoupling mechanism moving by means that the corresponding movable platform takes the decoupling connecting seat of the decoupling mechanism to perform a corresponding reciprocating motion together; thereby, the two movable mechanisms cooperate to enable the decoupling mechanism take the orthopedic surgical tool held by the clamper to a predetermined position within a motion range thereof;
    each of the two movable mechanism also comprises a limit switch and limit blocks; the limit switch is installed on the base, and the limit blocks are arranged at both ends of the corresponding movable platform and cooperate with the corresponding limit switch for limiting a motion position of the corresponding movable platform;
    each of the two movable mechanisms further comprises a grating ruler and a reading head, the grating ruler is arranged along a motion route of the corresponding movable platform, position information is obtained by the reading head, and the grating ruler and the reading head cooperate with each other to detect a position of the corresponding movable platform, the clamping mechanism is connected to the decoupling mechanism; the decoupling mechanism is connected to the two movable mechanisms; and the two movable mechanisms cooperate to—enable the orthopedic surgical tool to reach any position within a motion range.

2. The orthopedic surgical device of claim 1, wherein:
    the two movable mechanisms are installed on the same base;
    the linear motors of the two movable mechanisms are installed at different positions on the same base;
    the base is an integral structure; and
    the base is T-shaped, L-shaped or cross-shaped.

3. The orthopedic surgical device of claim 1, wherein:
    the two movable mechanisms are selected from: a horizontal movable mechanism, a depth movable mechanism, and a vertical movable mechanism; the horizontal movable mechanism provides a reciprocating motion variable in the horizontal direction; the depth movable mechanism provides a reciprocating motion variable in the depth direction; and the vertical movable mechanism provides a reciprocating motion variable in the vertical direction.

4. The orthopedic surgical device of claim 1, wherein:
    the decoupling mechanism further comprises a decoupling guide rail; the decoupling guide rail is installed on the mounting seat, and is provided with a sliding block; the sliding block is slidable along the decoupling guide rail without dispatching off the decoupling guide rail;

the decoupling connecting seat is connected to the sliding block, and is slidable relative to the decoupling guide rail by means of the sliding block;

the mounting seat is relatively movably or fixedly connected with the movable platform of one of the two movable mechanisms, while the decoupling connecting seat is relatively movably or fixedly connected with the movable platform of the other of the two movable mechanisms.

5. The orthopedic surgical device of claim 1, wherein:

the mounting seat is relatively slidably connected with the movable platform of one movable mechanism, a front side of the movable platform of the one movable mechanism is provided with the linear guide or cross-roller guide; the mounting seat is installed to the front side of the movable platform, and is capable of performing a reciprocating motion on the front side of the movable platform along the linear guide or the cross-roller guide; a back side of the movable platform is connected to the mover of the linear motor of the one movable mechanism; and the decoupling connecting seat is fixedly connected with the movable platform of the other movable mechanism.

6. The orthopedic surgical device of claim 1, wherein:

the clamping mechanism clamper comprises a tool clamp, a tool clamp seat and a sensor; the tool clamp seat and the tool clamp are fixed together for clamping the orthopedic surgical tool therebetween; the sensor is installed between the mounting seat of the decoupling mechanism and the tool clamp seat, and used to detect forces and torques of various directions during the orthopedic surgical tool work.

7. The orthopedic surgical device of claim 6, wherein:

the tool clamp and the tool clamp seat are connected to each other by guide posts;

the sensor is a six axis six-axes sensor, which and is electrically connected to a surgical robot or a control center;

the base of the movable mechanisms is provided with an interface seat for a flange connection with an arm of the surgical robot.

8. An orthopedic surgical robot system, comprising:

a surgical robot; and the orthopedic surgical device of claim 1, connected to the surgical robot.

9. The orthopedic surgical robot system of claim 8, wherein:

the orthopedic surgical robot comprises a control center of the system, the linear motor is connected to the control center; the orthopedic surgical tool is provided with a navigation surface recognizable by a vision system, the orthopedic surgical robot system further comprises a binocular vision system, the binocular vision system is capable of recognizing the navigation surface.

* * * * *